US011058672B2

(12) United States Patent
Motheram et al.

(10) Patent No.: US 11,058,672 B2
(45) Date of Patent: Jul. 13, 2021

(54) PHARMACEUTICAL COMPOSITIONS AND METHODS FOR PRODUCING LOW IMPURITY CONCENTRATIONS OF THE SAME

(71) Applicant: Chiesi Farmaceutici S.p.A., Parma (IT)

(72) Inventors: Rajeshwar Motheram, Dayton, OH (US); Gopal Krishna, Randolph, NJ (US); Min Ding, Tarrytown, NY (US); Keith Flood, Cary, NC (US); Kornepati Ramakrishna, Cary, NC (US)

(73) Assignee: CHIESI FARMACEUTICA S.P.A., Parma (IT)

(*) Notice: Subject to any disclaimer, the term of this patent is extended or adjusted under 35 U.S.C. 154(b) by 0 days.

(21) Appl. No.: 16/197,647

(22) Filed: Nov. 21, 2018

(65) Prior Publication Data
US 2019/0091212 A1    Mar. 28, 2019

Related U.S. Application Data

(63) Continuation of application No. 13/919,893, filed on Jun. 17, 2013, now abandoned, which is a continuation of application No. 13/600,056, filed on Aug. 30, 2012, now abandoned, which is a continuation of application No. 12/511,631, filed on Jul. 29, 2009, now abandoned.

(60) Provisional application No. 61/093,772, filed on Sep. 3, 2008, provisional application No. 61/085,597, filed on Aug. 1, 2008.

(51) Int. Cl.
A61K 31/4422 (2006.01)
A61K 31/519 (2006.01)
G01N 30/02 (2006.01)

(52) U.S. Cl.
CPC ........ *A61K 31/4422* (2013.01); *A61K 31/519* (2013.01); *G01N 30/02* (2013.01)

(58) Field of Classification Search
CPC combination set(s) only.
See application file for complete search history.

(56) References Cited

U.S. PATENT DOCUMENTS

| 4,150,744 | A |   | 4/1979 | 7Ennimore et al. |
|-----------|---|---|--------|------------------|
| 4,693,892 | A |   | 9/1987 | Legasy et al. |
| 5,714,520 | A |   | 2/1998 | Jones et al. |
| 5,739,152 | A | * | 4/1998 | Andersson ........... A61P 9/00 514/356 |
| 5,856,346 | A |   | 1/1999 | Andersson et al. |
| 6,350,877 | B1 |  | 2/2002 | Mattson et al. |
| 8,658,676 | B2 |  | 2/2014 | Motheram et al. |
| 10,010,537 | B2 | | 7/2018 | Motheram et al. |
| 2003/0119883 | A1 | | 6/2003 | Bentham et al. |
| 2005/0186230 | A1 | | 8/2005 | Chen et al. |
| 2005/0272763 | A1 | | 12/2005 | Toupence et al. |
| 2005/0276824 | A1 | | 12/2005 | Wang et al. |
| 2006/0047125 | A1 | | 3/2006 | Leonardi et al. |
| 2006/0160834 | A1 | | 7/2006 | Fong et al. |
| 2007/0196465 | A1 | | 8/2007 | Bobotas et al. |
| 2008/0019978 | A1 | | 1/2008 | Palani et al. |
| 2010/0113534 | A1 | | 5/2010 | Motheram et al. |

FOREIGN PATENT DOCUMENTS

| CN | 101766568 A | 7/2010 |
| CN | 101780036 A | 7/2010 |
| EP | 1813274 B1 | 8/2007 |
| EP | 1813274 B1 | 12/2009 |
| EP | 2320740 B1 | 3/2014 |
| JP | 2003-104888 A | 4/2003 |
| WO | 9513066 A1 | 5/1995 |
| WO | 0031035 A1 | 6/2000 |
| WO | 0057885 A1 | 10/2000 |
| WO | 2006118210 A1 | 11/2006 |
| WO | 2010022259 A1 | 2/2010 |

OTHER PUBLICATIONS

Nordlander et al., "Pharmacodynamic, Pharmacokinetic and Clinical Effects of Clevidipine, an Ultrashort-acting Calcium Antagonist for Rapid Blood Pressure Control.", Cardiovascular Drug Reviews, vol. 22, No. 3, (2004), pp. 227-250, URL: http://lwww.edictforpressurecontrol.com/pdf/NorlanderCardiovascDrugRev.pdf, XP008142879 http://dx.doi.org/10.1111/j.1527-3466.2004.tb00143.x.

Gyllenhall et al., "Packed-column supercritical fluid chromatography for the purity analysis of clevidipine, a new Jihyrdopyridine drug.", Journal of Chromatography A, (1999), vol. 862, No. ISS 1, pp. 95-104, XP009150407.

The English translation of the Japanese Office Action, dated Sep. 10, 2013, in the corresponding Japanese Patent Application No. 2011-521291.

Okano, "New Pharmaceutical Review," published by Nankodo, 1987, 3rd edition, pp. 364 and 370-371. (English translation).

Gyllenhaal et al., "Packed-column supercritical fluid chromatography for the purity analysis of clevidipine, a new dihydropyridine drug," Journal of Chromatography A, vol. 862, Issue 1, Nov. 5, 1999, pp. 95-104.

Levy et al., "Clevidipine effectively and rapidly controls blood pressure preoperatively in cardiac surgery patients: the results of the randomized, placebo-controlled efficacy study of clevidipine assessing its preoperative antihypertensive effect in cardiac surgery-1," Anesth Analg. Oct. 2007;105(4):918-25.

The English translation of the Japanese Office Action, dated Oct. 8, 2013, in the related Japanese application 2011-521123.

(Continued)

*Primary Examiner* — Kortney L. Klinkel
*Assistant Examiner* — Tori Strong
(74) *Attorney, Agent, or Firm* — Maryellen Feehery Hank; Vorys, Sater, Seymour and Pease LLP

(57) ABSTRACT

A composition having clevidipine as an active ingredient is described. The composition includes clevidipine as an active ingredient and an amount of the impurity H168/79 that is no greater than about 1.5%, or where the ratio between clevidipine and H168/79 is equal or above 60 to 1.

11 Claims, 1 Drawing Sheet

(56) References Cited

OTHER PUBLICATIONS

Gyllenhaal et al., "Packed-column supercritical fluid chromatography for the purity analysis of clevidipine, a new drug," Journal of Chromatography A, vol. 862, Issue 1, Nov. 5, 1999, pp. 95-104.
STN Entry for Clevidipine and metabolites, RN 167221-71-8, RN 123853-39-4, and RN 188649-48-1, all entered 1997 or earlier, 3 pages.
Riaz, Causes of high blood pressure/Hypertension, 2011, http://www.highbloodpressuremed.com/causes-of-high-blood-pressure-hypertension.html, accessed Jul. 13, 2011.
The English translation of the Japanese Office Action, dated Oct. 8, 2013, in the related Japanese application No. 2011-521123.
The extended European Search Report by the European Patent Office, dated Jul. 26, 2011, in related European patent application No. 09803270.9.
The extended European Search Report by the European Patent Office, dated Nov. 2, 2011, in related European patent application No. 09803550.4.
The International Search Report and Written Opinion by the International Searching Authority, issued on Sep. 22, 2009, in related PCT application No. PCT/US09/04399.
Jaremo et al., "Supercritical Fluid Extraction of Clevidipine from a Water Based Vegetable Oil Emulsion," Journal of Liquid Chromatography & Related Technologies, vol. 21, Issue 3, 1998, pp. 391-406.
Office Actions dated Jun. 28, Jul. 28 and Sep. 30, 2011 in the related U.S. Appl. No. 12/462,147.
The International Search Report and Written Opinion by the International Searching Authority, dated Sep. 25, 2009, in the PCT application No. PCT/US09/52127.
Gyllenhall et el, "Packed-column supercritical fluid chromatography for the purity analysis of clevidipine, a new dihydropyridine drug," Journal of Chromatography A, vol. 862, Issue 1, Nov. 5, 1999, pp. 95-104.
Mirtallo et al., "State of the art review: Intravenous fat emulsions: Current applications, safety profile, and clinical Implications," Ann Pharmacother. Apr. 2010;44(4):688-700.
Ericsson et al., "In vitro hydrolysis rate and protein binding of clevidipine, a new ultrashort-acting calcium antagonist metabolised by esterases, in different animal species and man," Eur J Pharm Sci. Apr. 1998;8(1):29-3T.
Zhang et al., "Short Communication Human Cytochrome P450 Induction and Inhibition Potential of Clevidipine and Its Primary Metabolite H152/81," DMD May 2006 vol. 34 No. 5 734-737.
Ericsson et al., "Pharmacokinetics and pharmacodynamics of clevidipine in healthy volunteers after intravenous nfusion," Eur J Clin Pharmacol. Mar. 1999;55(1):61-7.
Mang, "Clevidipine (the Medicines Company)," Curr Opin Investig Drugs. Oct. 2002;3(10):1474-8.
Cleviprex Bibliography maintained by the Medicines Company, May 2011.
Cada et al., "Clevidipine Butyrate Injectable Emulsion," Hospital Pharmacy, 2008; vol. 43, No. 11, 903-912.
Huraux C., et al., "H324/38, a new ultrashort acting calcium channel blocker: evaluation of its vasodilator effect in vitro", Anesthesiology 1996; 85 (3A): A123.
ICH Harmonized tripartite guideline specifications: test procedures and acceptance criteria for new drug substances and new drug products: chemical substances,Q6A, Current step 4 version dated Oct. 6, 1999.
Handbook of pharmaceutical excipients 4th ed Published in 2003 pp. 225-228 546-548 and 560-562.

* cited by examiner

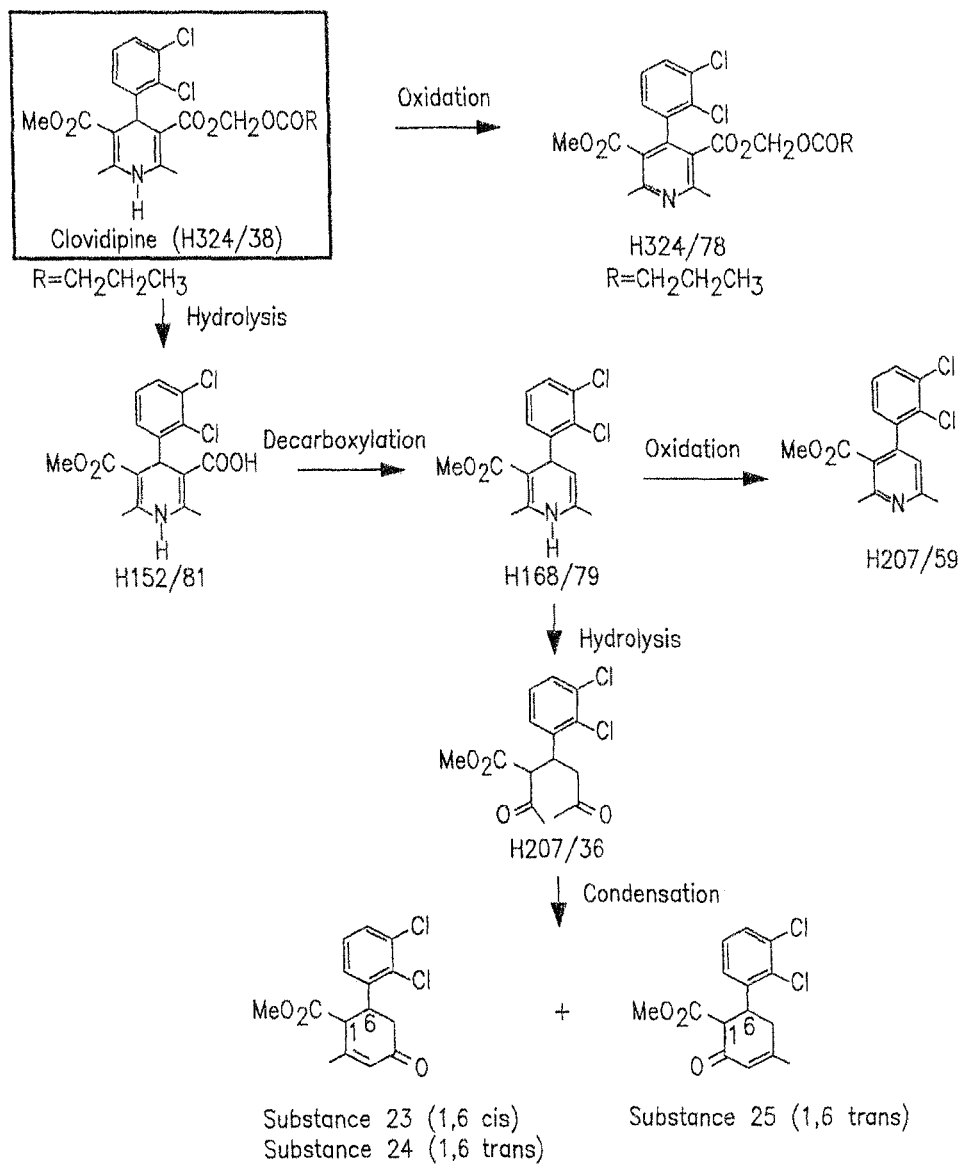

PHARMACEUTICAL COMPOSITIONS AND METHODS FOR PRODUCING LOW IMPURITY CONCENTRATIONS OF THE SAME

This application is a continuation of U.S. application Ser. No. 13/919,893, filed on Jun. 17, 2013, which is a continuation of U.S. application Ser. No. 13/600,056, filed on Aug. 30, 2012, which is a continuation of U.S. application Ser. No. 12/511,631, filed on Jul. 29, 2009, which claims priority from U.S. Provisional Patent Application No. 61/093,772 filed on Sep. 3, 2008, and U.S. Provisional Patent Application No. 61/085,597 filed on Aug. 1, 2008 the entire contents of both applications are hereby expressly incorporated by reference herein.

FIELD OF THE INVENTION

The instant invention relates to pharmaceutical compositions, and in particular to compositions of clevidipine having a reduced level of impurities, and a method of maintaining the stability of such pharmaceutical compositions.

BACKGROUND OF THE INVENTION

Clevidipine, which is also known as Cleviprex™, is a short-acting, vascular selective calcium antagonist that has been shown to reduce arterial blood pressure with a fast termination of effect due to metabolism by blood and tissue esterases. As an arterial-selective vasodilator, clevidipine reduces peripheral vascular resistance directly, without dilating the venous capacitance bed.

The chemical name of clevidipine is butyroxymethyl methyl 4-(2',3'-dichlorophenyl)-1,4-dihydro-2,6-dimethyl-3,5-pyridinedicarboxylate ($C_{21}H_{23}Cl_2NO_6$). Its structure is as follows:

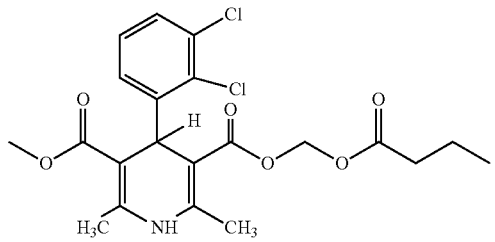 [SMILES: CCCC(=O)OCOC(=O)C1=C(C)NC(C)=C(C(=O)OC)C1c1cccc(Cl)c1Cl]

Clevidipine is typically formulated as a liquid emulsion suitable for intravenous administration. Lipid emulsions are widely used in parenteral nutrition use for approximately 30 years and in the recent past have been used as drug carriers for insoluble drugs such as propofol (Diprivan®), and diazepam. Apart from their ability to deliver insoluble drugs, emulsions are also suitable dosage forms for drugs like clevidipine that are susceptible to hydrolytic breakdown. Emulsions have also been reported to prevent drugs from adhering to plastic administration sets used during intravenous injection, and reduce local toxicity on infusion.

As a pharmaceutical composition, it is essential that clevidipine maintains its stability. Over the past several years, various impurities have been identified in compositions containing clevidipine as an active ingredient. For example, some impurities arise from the process used in making clevidipine, while others are due to gradual degradation of the active ingredient. As a pharmaceutical composition, it is essential to maintain stability and minimize the amount of impurities regardless of their source or the mechanism of degradation. Therefore, a need exists for compositions of clevidipine having acceptable stability profiles with respect to their ultimate potency and impurity levels. There is also a need for methods for maintaining the stability of compositions having clevidipine as an active ingredient.

SUMMARY OF THE INVENTION

The first aspect of the present invention describes a number of impurities which may be derived from clevidipine through a hydrolysis, decarboxylation and condensation reaction. It describes the structure of these impurities and methods of detecting and analyzing these impurities.

The second aspect of the present invention describes methods of reducing the amount of such impurities in a pharmaceutical compositions having clevidipine as an active ingredient.

The third aspect of the present invention describes pharmaceutical compositions prepared or stored using the methods described herein wherein the level of certain impurities is minimized or reduced, In particular, the present invention describes pharmaceutical composition having clevidipine as an active ingredient, and having a reduced level of one or more impurities selected from a group consisting of Substance 23, Substance 24, Substance 25 and H168/79.

More specifically, the present invention describes a pharmaceutical composition having clevidipine as an active ingredient, wherein the compositions contains equal or no more than 0.2% of an impurity on a weight-to-weight of impurity to clevidipine and the impurity is selected from a group consisting of Substance 23, 24 and 25.

Even more specifically, the present invention describes a pharmaceutical composition having clevidipine or any of its pharmaceutically acceptable salt forms, as the active ingredient, wherein the composition contains equal or no more than 0.2% on a weight-to-weight of impurity to clevidipine for each of the purities, Substance 23, 24 and 25.

The present invention includes compositions having clevidipine, as an active ingredient, wherein the composition contain a reduced level of an amount of the impurity H168/79 that is no greater than about 1.5% weight-to-weight of impurity to clevidipine basis, or where the ratio of the area under the chromatographic curve between clevidipine and H168/79 is equal or greater than 60 to 0.9.

The present invention also includes compositions having clevidipine or any of its pharmaceutical acceptable salt forms, as an active ingredient, wherein the compositions contain a reduced level of an amount of the impurities H168/79, Substance 23, Substance 24, and Substance 25 that the level of H168/79 is no greater than about 1.5% on a weight-to-weight of impurity to clevidipine or where the ratio of the area under the chromatographic curve between clevidipine and each of Substance 23, Substance 24, and/or Substance 25 is equal or greater than 500 to 1, and the ratio the area under the chromatographic curve between clevidipine and H168/79 is equal or greater than 60 to 0.9.

The present invention also describes a method of manufacturing compositions having clevidipine as an active ingredient, and an amount of the impurity H168/79 that is no greater than about 1.0% weight-to-weight of impurity to clevidipine, or where the ratio between clevidipine and H168/79 is equal or greater than 100 to 1.

The fourth aspect of the present invention is a method of treating or alleviating a disease or condition in a subject in need thereof, comprising administering to the subject an effective amount of a pharmaceutical composition having clevidipine or any of its pharmaceutical acceptable salt forms as the active ingredient, wherein the level of impurities is reduced or minimized to no more than 0.2% weight-to-weight of impurity to clevidipine for any of Substance 23, Substance 24, and Substance 25, and no more than 1.5% for H168/79 based on a weight-to-weight of impurity to clevidipine. As used herein the disease or condition refers to any disease or condition which may be treated using a selective calcium channel block, such as clevidipine. Examples of such disease or condition include, without limitation, hypertension, such as primary hypertension, secondary hypertension, acute hypertension, chronic hypertension, high blood Pressure, chest pain (angina), migraine, brain aneurysm complications, irregular heartbeats (arrhythmia) and Raynaud's disease.

DESCRIPTION OF THE FIGURES

Understanding of the present invention will be facilitated by consideration of the following detailed description of the embodiments of the present invention taken in conjunction with the accompanying drawing, in which like numerals refer to like parts and in which:

FIG. 1 illustrates a proposed degradation pathway of clevidipine.

DETAILED DESCRIPTION OF THE PREFERRED EMBODIMENTS

It is to be understood that the figures and descriptions of the present invention have been simplified to illustrate elements that are relevant for a clear understanding of the present invention, while eliminating, for the purpose of clarity, many other elements found in typical pharmaceutical compositions and methods of stabilization. Those of ordinary skill in the art will recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Furthermore, the embodiments identified and illustrated herein are for exemplary purposes only, and are not meant to be exclusive or limited in their description of the present invention.

As mentioned previously, clevidipine is a fast acting dihydropyridine calcium channel blocking agent developed for the treatment of various conditions, such as hypertension, including primary hypertension, secondary hypertension, acute hypertension, chronic hypertension and perioperative hypertension in cardiac surgery, high blood pressure, chest pain (angina), migraines, brain aneurysm complications, irregular heartbeats (arrhythmia) and Raynaud's disease. As an arterial-selective vasodilator, clevidipine reduces peripheral vascular resistance directly, without dilating the venous capacitance bed. The end effect can be a reduction in systolic blood pressure. More detailed information on short-acting dihydropyridines and their clinical indications can be found in U.S. Pat. No. 5,856,346, the entire disclosure of which is incorporated by reference herein as if set forth in its entirety.

As used herein, the term "clevidipine" shall mean and include all varieties of forms of clevidipine. Unless otherwise specified, examples of such forms include all pharmaceutically acceptably salts, esters, isomers, stereo isomers, crystalline and amorphous forms.

As used herein, the term "pharmaceutically acceptable salt" shall refer to salts prepared from pharmaceutically acceptable non-toxic bases or acids including inorganic or organic bases and inorganic or organic acids. Examples of salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Clevidipine is manufactured by reaction of 4-(2',3'-dichlorophenyl)-1,4-dihydro-5-methoxycarbonyl-2,6-dimethyl-3-pyridinecarboxylic acid with chloromethyl butyrate to obtain clevidipine. This reaction can be done optionally in the presence of a corresponding hydrogen carbonate, such as $KHCO_3$, in refluxing acetonitrile. Inorganic salts can be removed by filtration and the product is crystallized by the addition of isopropanol and water with subsequent cooling. It can also be crystallized by exchanging solvent from acetonitrile to a mixture of alcohol, such as ethanol or isopropanol, and water with repeated evaporations. In the further purification of the product the crystals are washed with a mixture of water and ethanol or isopropanol. The product can be dissolved in refluxing isopropanol, crystallized by cooling, isolated by filtration and finally washed with a water and isopropanol mixture. A more detailed description of the manufacturing process of clevidipine can be found in U.S. Pat. No. 6,350,877, the entire disclosure of which is incorporated by reference herein as if set forth in its entirety.

Clevidipine is practically insoluble in water, and thus is typically formulated as a liquid emulsion suitable for intravenous administration. Typically, each mL may contain 0.5 mg clevidipine in approximately 20% soybean oil emulsion for intravenous administration. Other ingredients may include glycerin, water, purified egg yolk phospholipids, and sodium hydroxide to adjust pH.

Emulsions offer much better solubility, less side effects of the vehicle and better stability than conventional solutions. Oil-in-water emulsions also prevent the compound from adherence to plastic infusion sets that are to be used when administering the compound. These emulsions provide a fast release and decay, and offer much better in vivo solubility properties, fewer side effects of the vehicle and better stability than conventional solutions. Further information regarding the formulation of clevidipine can be found in U.S. Pat. No. 5,739,152, the entire disclosure of which is incorporated by reference herein as if set forth in its entirety.

It was previously unknown that compositions having clevidipine as an active ingredient are heat intolerant and sensitive to water content. However, based on this discovery that such adverse conditions can give rise to an unacceptable level of impurities from pharmaceutical compositions having clevidipine as an active ingredient, the present invention provides compositions that include clevidipine and minimized impurity levels, along with methods of manufacturing and preserving these pharmaceutical compositions.

It has been discovered that clevidipine degrades under adverse conditions into several impurities that compromise the purity and ultimately the potency of clevidipine. For example, under adverse conditions, clevidipine metabolizes into H168/79, which is also called methyl 4-(2',3'-dicloropenyl)-1,4-dihydro-2,6,-dimethyl-5-pyridine-carboxylate, and is shown in the following formula:

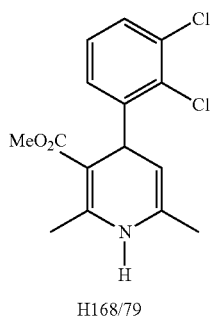

H168/79

Based on this discovery, a degradation pathway of clevidipine is proposed, and is shown in FIG. 1. This pathway includes a number of clevidipine degradation products, such as H324/78, H152/66, H152/81, H168/79, H207/59, and H207/36, for example. The pathway also illustrates the further degradation of H168/79, by way of hydrolysis and condensation, into Substance 23, Substance 24, and/or Substance 25. The composition of Substance 23, Substance 24, and Substance 25 is as follows:

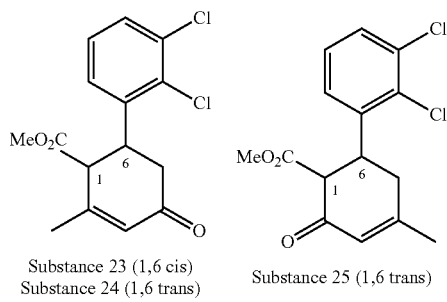 [SMILES: COC(=O)C1C(C)=CC(=O)CC1c1cccc(Cl)c1Cl ; COC(=O)C1C(=O)C=C(C)CC1c1cccc(Cl)c1Cl]

Substance 23 (1,6 cis)
Substance 24 (1,6 trans)

Substance 25 (1,6 trans)

Impurity levels were evaluated to determine the stability of clevidipine emulsions and their ability to minimize degradation of clevidipine under exposure to light. In addition H152/81, H168/79 and H207/59 are metabolites of clevidipine. H324/78 is a pyridine analog of the active ingredient and is formed by the oxidation of clevidipine. Degradation product H152/81 is a dihydropyridine carboxylic acid and is formed from the hydrolysis of clevidipine. H152/81 can undergo decarboxylation and oxidation sequentially to form H168/79 and H207/59 respectively. The degradation product H168/79 can undergo hydrolysis to form the diketo ester H207/36 which can further cyclize to form substituted cyclohexenone derivative impurities such as Substance 23 and Substance 25. Substance 24, a diastereomer of Substance 23, may also form during this reaction.

As with any of the exemplary embodiments of pharmaceutical compositions described herein, it is preferred that the level of impurities in the composition is as low as possible. Therefore, while various exemplary embodiments of pharmaceutical compositions include amounts of impurities within acceptable and effective ranges for the compositions as a whole, the more pure the composition, meaning the higher the percent of clevidipine or any of its acceptable salt forms, the better.

Substance 23 is an impurity generated through the degradation of H168/79. The degradation of H168/79 is accelerated when exposed to temperatures in excess of 25° C. as compared to temperatures below 5° C. Therefore, the level of Substance 23 increases at higher temperatures.

Similarly, Substance 25 is an impurity generated through the degradation of H168/79 and may increase in quantity as H168/79 degrades.

Previously unidentified Substance 24 is also a degradation product of H168/79. Given that Substance 24 is a diastereomer of Substance 23, a separate HPLC method was developed to validate and quantify Substance 24.

The present invention further includes a method of identifying and quantifying levels of Substance 24 in pharmaceutical samples having clevidipine as an active ingredient. In one embodiment, the method of detecting Substance 24 in pharmaceutical samples having clevidipine as an active ingredient includes the step of isolating the individual chemical compounds making up the degradants or impurities found in the clevidipine degradation pathway. This can be accomplished by column chromatography, such as high pressure liquid chromatography ("HPLC"), for example. The pharmaceutical sample having clevidipine as an active ingredient can introduced in small volume to the column and the resulting analysis of the eluent may illustrate the isolation and identification of peaks representative of Substance 24. As may be understood by those skilled in the art, any optimization of the HPLC method may be performed to give the best separation of peaks as between the various impurities found in the degradation of clevidipine. Typical HPLC methods useful in the present invention are presented in Examples 1 and 2. Based on this method of detecting Substance 24, the lower limit of detection, or the minimum detectible level of Substance 24, may be approximately 0.01% area of the pharmaceutical composition containing clevidipine as an active ingredient. Alternatively, there could be a lower limit of Substance 24, where the ratio of clevidipine to Substance 24 may be equal or similar to 9000 to 1 which is equal to or similar to 0.01%. Similarly, the lower limit of Substance 25 or Substance 23 detection may be set forth as a ratio of clevidipine to Substance 25 or Substance 23, where the ratio of clevidipine to Substance 25 or Substance 23 may be equal or similar to 9000 to 1 which is equal to or similar to 0.01%.

Example 1 HPLC Procedure

Clevidipine assay and related substances were tested at each time point by a stability indicating method. This method is an isocratic, normal phase HPLC method with peak detection at 220 nm wavelength.

Column temperature: 35-40 degrees C.
Injection volume: 20 µl.
Flow rate: 1.0 ml/min.
Run time about 25 minutes.

Mobile phase of Heptane:ethanol (90:10) is employed and used for the assay of clevidipine and the degradation products with the exception of Substance 24.

Condition column with clevidipine mobile phase at 1.0 mL/min for 4 hours.

New column should be conditioned overnight at 0.2 mL/min.

When a degradation product is eluted, column can be washed with filtered ethanol for about 2 hours at 1.0 mL/min, then proceed with equilibration.

Examples of Column: PVA silica column 4.6 mm×150 mm, 5 micron PV12s051546WT or equivalent.

Example 2 HPLC Procedure Substance 24

This method is an isocratic, normal phase HPLC method with peak detection at 220 nm wavelength.

Column temperature: 35-40 degrees C.
Injection volume: 20 μl to 100 μl.
Run time about 60 minutes.
Mobile phase of Heptane:Isopropyl Alcohol (95:5) is employed is used for the assay of Substance 24.

Condition column with Heptane:Isopropyl Alcohol 95:5 mobile phase at 1.0 ml/min until the blank injection baseline is stable. New column should be conditioned overnight at 0.2 mL/min.

Examples of Column: Two PVA silica columns 4.6 mm×150 mm, 5 micron PV12s051546WT or equivalent.

Flow rate 1.0 mL/min.

Calculation of percent impurity based on total peak area:
Impurity Peak Area(100)
(total peak area of degradation products+H324/38 peak area (clevidipine peak area))

Calculation of percent impurity based on total peak area using H168/79 as the impurity example:
H168/79Peak Area(100)
(total peak area of degradation products+H324/38 peak area (clevidipine peak area))

When a standard of a particular decomposition product is available, quantization of the impurity may be accomplished by standard procedures known in the art such as constructing a standard curve or by calculating a relative response factor (RRF). When a standard is not available a ratio of the area under the curve for the impurity to clevidipine can be used assuming a RRF previously calculated or if the RRF is not known an RRF of 1.0 is used to calculate the percent impurity The present invention includes pharmaceutical compositions having clevidipine as an active ingredient, wherein the level of impurity H168/79 is no more than 1.5% on a weight-by-weight basis. In one embodiment of the present invention, the pharmaceutical composition includes clevidipine as an active ingredient and an amount of H168/79 that is no greater than about 1.2%. In other embodiments, the amount of H168/79 is preferably no greater than about 1.0%, and most preferably no greater than about 0.5%. These compositions may further include other degradants in variable amounts as described herein, provided the required level of potency of clevidipine remains satisfactory and effective for use to treat any indication as described or incorporated by reference herein.

The pharmaceutical composition exemplified in Tables 1, 2 and 3 are emulsions. The emulsions comprise: clevidipine 0.5 mg/ml, egg yolk phospholipid 1.2%, soybean oil 20%, glycerol 2.25%. The remainder being water adjusted to a pH between 6 and 8.8. The products were packaged in 100 ml glass type II bottles with 28 mm West compound 1821 black stopper and aluminum seal.

In another embodiment of the present invention, the pharmaceutical composition includes clevidipine as an active ingredient and H168/79, where the ratio of areas under the peak from an HPLC chromatogram between clevidipine and H168/79 is equal or above 60 to 0.9. Alternatively, the ratio between clevidipine and H168/79 can be equal to or above 100 to 1, 200 to 1, or 1000 to 1. In other embodiments, the ratio between clevidipine and H168/79 can be between 2000 to 1 and 1000 to 1. These compositions may further include other degradants in variable amounts as described herein, provided the required level of potency of clevidipine remains satisfactory and effective for use to treat any indication as described or incorporated by reference herein.

The percentage of H168/79 increases and stabilizes at lower temperatures approaching about 5° C., while it decreased at a temperatures approaching about 25° C. to about 40° C., for example. This trend shows that a higher temperatures, H168/79 undergoes further degradation to Substance 23, Substance 24, and/or Substance 25, by way of intermediary H207/36, as illustrated in FIG. 1.

Thus, as illustrated in Table 1, Table 2 and Table 3 below, the lowering of temperature also provides stability for H168/79 and, as a consequence, lowers and inhibits the amount of resulting second order impurities.

TABLE 1

| Percentage of H168/79 | | | | | | | | | | | |
|---|---|---|---|---|---|---|---|---|---|---|---|
| Time | KV 1322 | KV1328 | KV 1329 | TMC 001 | TMC 002 | | | | | | |
| 0 mo | 0.4 | 0.3 | 0.3 | 0.2 | 0.3 | | | | | | |
| | 5° C. upright | | | | | | 5° C. inverted | | | | |
| Time | KV 1322 | KV1328 | KV 1329 | TMC 001 | TMC 002 | Time | KV 1322 | KV1328 | KV 1329 | TMC 001 | TMC 002 |
| 3 mo | 0.1 | <0.1 | <0.1 | 0.1 | 0.1 | 3 mo | 0.2 | <0.1 | <0.1 | <0.1 | 0.2 |
| 6 mo | 0.2 | 0.1 | 0.1 | 0.2 | 0.2 | 6 mo | 0.2 | 0.1 | 0.1 | 0.2 | 0.2 |
| 9 mo | 0.3 | 0.1 | 0.3 | —[1] | 0.3 | 9 mo | 0.3 | 0.1 | 0.3 | 0.2 | 0.3 |
| 12 mo | 0.3 | —[1] | 0.5 | 0.3 | 0.5 | 12 mo | 0.3 | —[1] | 0.4 | 0.3 | 0.5 |
| 18 mo | 0.6 | 0.3 | 0.3 | 0.5 | 0.6 | 18 mo | 0.6 | 0.3 | 0.3 | 0.4 | 0.6 |
| 24 mo | 0.6 | 0.3 | 0.3 | 0.5 | 0.7 | 24 mo | 0.7 | 0.3 | 0.4 | 0.5 | 0.6 |
| 30 mo | 0.6 | 0.4 | 0.3 | 0.5 | 0.7 | 30 mo | 0.6 | 0.4 | 0.4 | 0.5 | 0.7 |

TABLE 1-continued

Percentage of H168/79

| | 25° C. upright | | | | | | 25° C. inverted | | | | |
|---|---|---|---|---|---|---|---|---|---|---|---|
| Time | KV 1322 | KV1328 | KV 1329 | TMC 001 | TMC 002 | Time | KV 1322 | KV1328 | KV 1329 | TMC 001 | TMC 002 |
| 3 mo | 0.8 | 0.5 | 0.4 | 0.7 | 1.0 | 3 mo | 0.8 | 0.5 | 0.4 | 0.7 | 1.0 |
| 6 mo | 0.7 | 0.4 | 0.4 | 0.5 | 0.9 | 6 mo | 0.6 | 0.4 | 0.3 | 0.3 | 0.9 |
| 9 mo | 0.5 | 0.4 | 0.4 | 0.5 | —[1] | 9 mo | 0.5 | 0.4 | 0.4 | —[1] | 0.8 |
| 12 mo | 0.4 | —[1] | 0.4 | 0.4 | 0.5 | 12 mo | 0.4 | —[1] | 0.4 | 0.4 | 0.5 |
| 18 mo | 0.4 | 0.3 | 0.2 | 0.4 | 0.5 | 18 mo | 0.4 | 0.3 | 0.2 | 0.5 | 0.5 |
| 24 mo | 0.3 | 0.3 | 0.2 | 0.3 | 0.4 | 24 mo | 0.3 | 0.3 | 0.2 | 0.3 | 0.4 |

| | 40° C. upright | | | | | | 20° C. inverted | | | | |
|---|---|---|---|---|---|---|---|---|---|---|---|
| Time | KV 1322 | KV1328 | KV 1329 | TMC 001 | TMC 002 | Time | KV 1322 | KV1328 | KV 1329 | TMC 001 | TMC 002 |
| 1 mo | 0.9 | 0.6 | 0.4 | 0.9 | 1.2 | 1 mo | 0.9 | 0.6 | 0.4 | 0.9 | 1.3 |
| 2 mo | 0.6 | —[1] | 0.3 | 0.6 | 1.1 | 2 mo | 0.7 | —[1] | 0.3 | 0.7 | 1.0 |
| 3 mo | 0.4 | 0.3 | 0.3 | 0.5 | 0.8 | 3 mo | 0.4 | 0.3 | 0.3 | 0.5 | 0.7 |
| 6 mo | 0.3 | 0.2 | 0.2 | 0.6 | 0.4 | 6 mo | 0.3 | 0.3 | 0.2 | 0.3 | 0.4 |

TABLE 2

Percentage of Substance 23

| Time | KV 1322 | KV1328 | KV 1329 | TMC 001 | TMC 002 |
|---|---|---|---|---|---|
| 0 mo | ND | ND | ND | ND | ND |

| | 5° C. upright | | | | | | 5° C. inverted | | | | |
|---|---|---|---|---|---|---|---|---|---|---|---|
| Time | KV 1322 | KV1328 | KV 1329 | TMC 001 | TMC 002 | Time | KV 1322 | KV1328 | KV 1329 | TMC 001 | TMC 002 |
| 3 mo | ND | ND | ND | ND | ND | 3 mo | ND | ND | ND | ND | ND |
| 6 mo | 0.1 | ND | ND | ND | ND | 6 mo | <0.1 | ND | ND | ND | ND |
| 9 mo | ND | ND | ND | —[1] | ND | 9 mo | ND | ND | ND | ND | ND |
| 12 mo | ND | —[1] | ND | ND | ND | 12 mo | ND | —[1] | ND | ND | ND |
| 18 mo | ND | ND | <0.1 | ND | ND | 18 mo | ND | ND | ND | ND | ND |
| 24 mo | <0.1 | ND | ND | <0.1 | <0.1 | 24 mo | <0.1 | ND | <0.1 | <0.1 | <0.1 |
| 30 mo | <0.1 | <0.1 | ND | ND | ND | 30 mo | ND | <0.1 | ND | ND | ND |

| | 25° C. upright | | | | | | 25° C. inverted | | | | |
|---|---|---|---|---|---|---|---|---|---|---|---|
| Time | KV 1322 | KV1328 | KV 1329 | TMC 001 | TMC 002 | Time | KV 1322 | KV1328 | KV 1329 | TMC 001 | TMC 002 |
| 3 mo | ND | ND | ND | <0.1 | 0.1 | 3 mo | <0.1 | ND | ND | <0.1 | 0.1 |
| 6 mo | 0.2 | <0.1 | ND | 0.2 | 0.3 | 6 mo | 0.2 | ND | ND | 0.3 | 0.3 |
| 9 mo | 0.3 | 0.1 | ND | 0.3 | —[1] | 9 mo | 0.4 | 0.1 | ND | —[1] | 0.4 |
| 12 mo | 0.4 | —[1] | 0.1 | 0.4 | 0.6 | 12 mo | 0.4 | —[1] | 0.1 | 0.4 | 0.6 |
| 18 mo | 0.4 | 0.2 | 0.5 | 0.6 | 0.6 | 18 mo | 0.4 | 0.2 | 0.4 | 0.5 | 0.6 |
| 24 mo | 0.3 | 0.6 | 0.3 | 0.7 | 0.8 | 24 mo | 0.3 | 0.5 | 0.6 | 0.8 | 0.9 |

| | 40° C. upright | | | | | | 40° C. inverted | | | | |
|---|---|---|---|---|---|---|---|---|---|---|---|
| Time | KV 1322 | KV1328 | KV 1329 | TMC 001 | TMC 002 | Time | KV 1322 | KV1328 | KV 1329 | TMC 001 | TMC 002 |
| 1 mo | ND | ND | 0.1 | 0.1 | 0.1 | 1 mo | ND | ND | 0.1 | 0.1 | 0.1 |
| 2 mo | 0.2 | —[1] | 0.2 | 0.3 | 0.4 | 2 mo | 0.3 | —[1] | 0.1 | 0.3 | 0.4 |
| 3 mo | 0.4 | 0.3 | 0.2 | 0.4 | 0.6 | 3 mo | 0.3 | 0.2 | 0.2 | 0.4 | 0.5 |
| 6 mo | 0.8 | 0.6 | ND | 1.1 | 1.1 | 6 mo | 0.8 | 0.6 | ND | 0.9 | 1.0 |

TABLE 3

Percentage of Substance 25

| Time | KV 1322 | KV1328 | KV 1329 | TMC 001 | TMC 002 |
|---|---|---|---|---|---|
| 0 mo | ND | ND | ND | ND | ND |

| | 5° C. upright | | | | | | 5° C. inverted | | | | |
|---|---|---|---|---|---|---|---|---|---|---|---|
| Time | KV 1322 | KV1328 | KV 1329 | TMC 001 | TMC 002 | Time | KV 1322 | KV1328 | KV 1329 | TMC 001 | TMC 002 |
| 3 mo | ND | ND | ND | ND | ND | 3 mo | ND | ND | ND | ND | ND |
| 6 mo | <0.1 | ND | ND | ND | 0.3 | 6 mo | <0.1 | ND | ND | ND | 0.2 |

TABLE 3-continued

| Percentage of Substance 25 | | | | | | | | | | |
|---|---|---|---|---|---|---|---|---|---|---|
| 9 mo | ND | <0.1 | 0.1 | —[1] | 0.1 | 9 mo | ND | <0.1 | <0.1 | 0.1 | 0.1 |
| 12 mo | ND | —[1] | <0.1 | 0.1 | ND | 12 mo | ND | —[1] | <0.1 | 0.1 | ND |
| 18 mo | ND | ND | 0.1 | ND | ND | 18 mo | ND | ND | <0.1 | ND | ND |
| 24 mo | ND | ND | <0.1 | ND | <0.1 | 24 mo | ND | ND | <0.1 | ND | <0.1 |
| 30 mo | ND | <0.1 | ND | ND | ND | 30 mo | ND | <0.1 | ND | ND | ND |

| 25° C. upright | | | | | | 25° C. inverted | | | | |
|---|---|---|---|---|---|---|---|---|---|---|
| Time | KV 1322 | KV 1328 | KV 1329 | TMC 001 | TMC 002 | Time | KV 1322 | KV1328 | KV 1329 | TMC 001 | TMC 002 |
| 3 mo | ND | ND | ND | ND | ND | 3 mo | ND | ND | ND | ND | ND |
| 6 mo | <0.1 | ND | ND | <0.1 | 0.2 | 6 mo | <0.1 | ND | ND | ND | 0.2 |
| 9 mo | 0.1 | <0.1 | 0.1 | 0.1 | —[1] | 9 mo | 0.2 | <0.1 | <0.1 | —[1] | 0.2 |
| 12 mo | 0.2 | —[1] | 0.1 | 0.1 | 0.3 | 12 mo | 0.2 | —[1] | 0.1 | 0.1 | 0.3 |
| 18 mo | 0.3 | 0.2 | 0.1 | 0.3 | 0.3 | 18 mo | 0.2 | 0.2 | <0.1 | 0.3 | 0.4 |
| 24 mo | 0.4 | 0.3 | 0.3 | 0.4 | 0.5 | 24 mo | 0.3 | 0.3 | 0.3 | 0.4 | 0.5 |

| 40° C. upright | | | | | | 20° C. inverted | | | | |
|---|---|---|---|---|---|---|---|---|---|---|
| Time | KV 1322 | KV1328 | KV 1329 | TMC 001 | TMC 002 | Time | KV 1322 | KV1328 | KV 1329 | TMC 001 | TMC 002 |
| 1 mo | ND | ND | <0.1 | ND | ND | 1 mo | ND | ND | <0.1 | ND | ND |
| 2 mo | 0.1 | —[1] | <0.1 | 0.1 | <0.1 | 2 mo | 0.1 | NCR05833 | <0.1 | 0.1 | 0.2 |
| 3 mo | 0.2 | 0.2 | 0.2 | 0.1 | 0.2 | 3 mo | 0.2 | 0.2 | 0.2 | 0.1 | 0.2 |
| 6 mo | ND | 0.3 | 0.3 | 0.6 | 0.7 | 6 mo | <0.1 | 0.3 | 0.3 | ND | 0.6 |

According to an aspect of the present invention, the above mentioned methods of stabilizing pharmaceutical compounds having clevidipine as an active ingredient provide a shelf life of at least 36 months for the compositions, when stored at about 2° C. to 8° C. After being removed from this refrigerated condition and placed at roughly room temperature (15° C. to 30° C.), the compositions remain stable for up to at least 2 additional months.

The present invention also includes a method of maintaining the stability of a pharmaceutical composition having clevidipine as the active ingredient, including the slowing down or otherwise inhibiting of the hydrolysis pathway of clevidipine by reducing or inhibiting the amount of water in the process of manufacturing the composition, as well as the emulsification process in the final formulation.

In one embodiment of the present invention, clevidipine is manufactured by reaction of 4-(2',3'-dichlorophenyl)-1,4-dihydro-5-methoxycarbonyl-2,6-dimethyl-3-pyridinecarboxylic acid with chloromethyl butyrate to obtain clevidipine. This reaction can be done optionally in the presence of a corresponding hydrogen carbonate, such as KHCO₃, in refluxing acetonitrile. Inorganic salts can be removed by filtration and the product is crystallized by the addition of isopropanol with subsequent cooling. It can also be crystallized by exchanging solvent from acetonitrile to a mixture of alcohol, such as ethanol or isopropanol, with repeated evaporations. In the further purification of the product the crystals are washed with a mixture of ethanol or isopropanol. The product can be dissolved in refluxing isopropanol, crystallized by cooling, isolated by filtration and finally washed with an isopropanol mixture. A more detailed description of the manufacturing process of clevidipine can be found in U.S. Pat. No. 6,350,877, the entire disclosure of which is incorporated by reference herein as if set forth in its entirety.

Clevidipine is typically formulated as a liquid emulsion suitable for intravenous administration. Lipid emulsions are widely used in parenteral nutrition use for approximately 30 years and in the recent past have been used as drug carriers for insoluble drugs such as propofol (Diprivan®), and diazepam. Apart from their ability to deliver insoluble drugs, emulsions are also suitable dosage forms for drugs like clevidipine that are susceptible to hydrolytic breakdown. Emulsions have also been reported to prevent drugs from adhering to plastic administration sets used during intravenous injection, and reduce local toxicity on infusion.

Typically, each mL may contain 0.5 mg clevidipine in approximately 20% soybean oil emulsion for intravenous administration. Other ingredients may include glycerin, purified egg yolk phospholipids and sodium hydroxide to adjust pH. Generally, water for injection is dispensed to a mix tank at about 74° C. to about 78° C. Glycerin is added, and the aqueous phase is cooled to about 60° C. to about 70° C. prior to addition of the oil phase. For the oil phase, soybean oil is dispensed into a dissolving tank, mixed and heated to about 70° C. to about 82° C. Clevidipine is then added to the soybean oil mixture and heated to about 78° C. to about 82° C. Egg yolk phospholipids are then added to the mixture. The aqueous and oil phases are mixed together to form an emulsion, and the pH is adjusted with 1N sodium hydroxide to a pH of about 6 to about 8.8. The emulsion is then homogenized at a pressure of about 500 to 8000 psi and a temperature of about 50° C. to about 55° C. to a fine particle size. Preferably, the emulsion is homogenized at about 25° C., More preferably at about 15° C., still more preferably at about 10° C. and most preferably at about 5° C. The samples are filtered and dispensed into 50 mL or 100 mL bottles and capped with siliconized rubber stoppers, and crimp sealed with an aluminum overseal. Further information regarding the formulation of clevidipine can be found in U.S. Pat. No. 5,739,152, the entire disclosure of which is incorporated by reference herein as if set forth in its entirety.

Emulsions of the present invention comprise an oil-in-water emulsion comprising: a) clevidipine, b) a lipid phase, c) an emulsifier, and d) water or a buffer. The emulsion may also contain co-solvents or other solubility enhancers, anti-oxidants, stabilizers, pH-adjusting agents or tonicity modifying agents, such as glycerol.

In an emulsion of the present invention, clevidipine is present from about 0.4 mg/ml to about 0.6 mg/ml. Preferably clevidipine is present from abut 0.45 mg/ml to about 0.55 mg/ml. The lipid phase is present from about 1% to about 35%, preferably from about 18% to about 22%. The emulsifier is present from about 0.01 to about 2 times the weight of the lipid phase, preferably from about 0.5% to about 4% and more preferably from about 1% to about 1.32%. The remainder of the emulsion is water or buffer. The preferred range of water or buffer is about 75% to about 90%. The pH of the emulsion is adjusted to about 6 to about 8.8, preferably from about 7.5 to about 8.8. When present, glycerol is present from about 2% to about 2.5%. Percentages of the emulsion composition are expressed as weight/weight.

Lipid phases in the emulsion are any pharmaceutically acceptable oil, preferably triglycerides such as soy bean oil, safflower seed oil, olive oil, cottonseed oil, sunflower oil, sesame oil, peanut oil, corn oil, medium chain triglycerides (such as Miglyol® 812 or 810) or triacetin. The lipid phase may also be propylene glycol diesters or monoglycerides (such as acetylareal monoglycerides). The lipid phase can also be a mixture of said ingredients. The most preferred lipid phase is soy bean oil.

Emulsifiers are any pharmaceutically acceptable emulsifier, preferably phospholipids extracted from egg yolk or soy bean, synthetic phosphatidyl cholines or purified phosphatidyl cholines from vegetable origin. Hydrogenated derivatives can also be used, such as phosphatidyl choline hydrogenated (egg) and phosphatidyl choline hydrogenated (soya). Emulsifiers may also be non-ionic surfactants such as poloxamers (for example Poloxamer 188 and 407), poloxamines, polyoxyethylene stearates, polyoxyethylene sorbitan fatty acid esters or sorbitan fatty acid esters. Ionic suffactants may also be used such as cholic acid and deoxycholic acid or surface active deriviatives or salts thereof. The emulsifier can also be a mixture of said ingredients. The most preferred emulsifier is egg yolk phospholipid.

Those of ordinary skill in the art will recognize that many modifications and variations of the present invention may be implemented without departing from the spirit or scope of the invention. Thus, it is intended that the present invention cover the modification and variations of this invention provided they come within the scope of the appended claims and their equivalents.

The invention claimed is:

1. A method of reducing impurities in a composition comprising:
    heating an oil to between to about 70° C. to about 82° C.;
    adding to the heated oil clevidipine and heating the mixture to about 78° C. to about 82° C.;
    adding to the mixture egg yolk phospholipids; and
    adding an aqueous phase;
    wherein the pH is adjusted to about 6 to about 8.8;
    homogenizing the emulsion; and
    wherein the amount of degradant with the formula of:

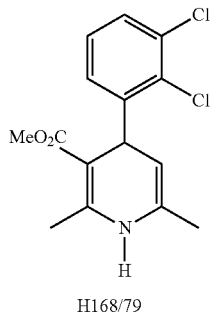

H168/79 is approximately equal to or less than about 1.5%.

2. The method of claim 1, wherein the amount of degradant H168/79 is approximately equal to or less than about 1.0%.

3. The method of claim 1, wherein the amount of degradant H168/79 is approximately equal to or less than about 0.5%.

4. A method of claim 1, wherein the aqueous phase consists essentially of glycerin.

5. The method of claim 1, wherein the mixture is homogenized at about 25° C.

6. The method of claim 1, wherein the mixture is homogenized at about 15° C.

7. The method of claim 1, wherein the mixture is homogenized at about 10° C.

8. The method of claim 1, wherein the mixture is homogenized at about 5° C.

9. A method of preparing and storing a pharmaceutical composition comprising:
    heating an oil to between to about 70° C. to about 82° C.;
    adding to the heated oil clevidipine and heating the mixture to about 78° C. to about 82° C.;
    adding to the mixture egg yolk phospholipids; and
    adding an aqueous phase;
    wherein the aqueous phase consists essentially of glycerin and the pH is adjusted to about 6 to about 8.8; and
    storing the composition at an effective temperature for at least 36 months wherein the amount of degradant with the formula of:

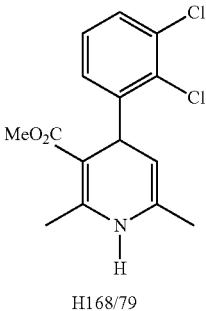

H168/79 is approximately equal to or less than about 1.5%.

10. The method of claim 9, wherein the amount of degradant is approximately equal to or less than about 1.0%.

11. The method of claim 9, wherein the amount of degradant is approximately equal to or less than about 0.5%.

* * * * *

UNITED STATES PATENT AND TRADEMARK OFFICE
CERTIFICATE OF CORRECTION

| | | |
|---|---|---|
| PATENT NO. | : 11,058,672 B2 | Page 1 of 1 |
| APPLICATION NO. | : 16/197647 | |
| DATED | : July 13, 2021 | |
| INVENTOR(S) | : Rajeshwar Motheram et al. | |

It is certified that error appears in the above-identified patent and that said Letters Patent is hereby corrected as shown below:

On the Title Page

Item (73), add:
HOSPIRA, INC., LAKE FOREST, IL (US)

Signed and Sealed this
Seventeenth Day of September, 2024

Katherine Kelly Vidal
*Director of the United States Patent and Trademark Office*